United States Patent
Benecke et al.

(10) Patent No.: US 10,125,079 B2
(45) Date of Patent: Nov. 13, 2018

(54) METHODS OF MAKING LEVULINIC ACID AND ALKYL LEVULINATES FROM SACCHARIDES

(71) Applicant: Battelle Memorial Institute, Columbus, OH (US)

(72) Inventors: Herman P. Benecke, Columbus, OH (US); Daniel B. Garbark, Blacklick, OH (US)

(73) Assignee: Battelle Memorial Institute, Columbus, OH (US)

( * ) Notice: Subject to any disclaimer, the term of this patent is extended or adjusted under 35 U.S.C. 154(b) by 0 days.

(21) Appl. No.: 15/403,751

(22) Filed: Jan. 11, 2017

(65) Prior Publication Data
US 2018/0194711 A1 Jul. 12, 2018

(51) Int. Cl.
*C07C 67/00* (2006.01)
*C07C 51/00* (2006.01)
*C07C 59/185* (2006.01)

(52) U.S. Cl.
CPC .............. *C07C 67/00* (2013.01); *C07C 51/00* (2013.01); *C07C 59/185* (2013.01)

(58) Field of Classification Search
CPC ........ C07C 59/185; C07C 67/00; C07C 51/00
See application file for complete search history.

(56) References Cited

U.S. PATENT DOCUMENTS

| | | | |
|---|---|---|---|
| 2,563,884 A | 5/1947 | Sugihara et al. | |
| 2,710,880 A | 6/1955 | Filachione et al. | |
| 3,267,136 A | 8/1966 | Vincenty et al. | |
| 4,721,780 A * | 1/1988 | McDaniel, Jr. | C07H 15/04 536/120 |
| 5,726,046 A | 3/1998 | Farone et al. | |
| 8,835,670 B2 | 9/2014 | Zhou et al. | |
| 2003/0233011 A1 | 12/2003 | Fagan et al. | |
| 2010/0179315 A1 | 7/2010 | Medoff | |
| 2013/0324708 A1* | 12/2013 | de Sousa Dias | C07C 67/00 536/18.6 |
| 2015/0045576 A1* | 2/2015 | Benecke | C07C 51/00 560/175 |
| 2016/0168070 A1* | 6/2016 | Saravanamurugan | C07C 51/09 435/146 |

FOREIGN PATENT DOCUMENTS

| EP | 0472474 A1 | 2/1992 |
|---|---|---|
| EP | 2184270 B1 | 12/2010 |

OTHER PUBLICATIONS

Kinetics of Acidic Hydrolysis of Raffinose; Zhong, Huisheng, Shipin Kexue (Beijing, China), 1989, 114, 1-4 (Abstract Only).
The Hydrolysis of Raffinose by Dilute Acids; de Grandchamp-Chaudun, Andree, Compt. Rend., 1953, 236, 244-6 (Language unavailable) (Abstract Only).
Annular Liquid Chromatograph for Reactions and Preparative Separations; Prior, Adalbert, Austrian, 1999, AT 405026, B1999426 (Abstract Only).
Comparative Polarographic Study of the Acid Hydrolysis of Some Sugars; Vina, J., et al., Revista Espanola de Fisiologia, 1961, 17, 131-5 (Abstract Only).
Capillary Electrophoresis as a Method for determining the Hydrolysis Rate Constant of Raffinose; Ding, Xianghuan, at al., Journal of Electrophoresis and Microchip Technology, 2002, 7 (3 & 4), 87-90 (English) (Abstract only).
Preparation of Melibiose and D-Fructose by Hydrolysis of Raffinose; Kubala, Jozef and Ondrejkovic, Anton, Czech, 1987, CS 239597 B1 19860116, (Abstract Only).
Descending Paper Chromatography of Oligosacchrides; Border, C.L., Jr., Journal of Chemical Education, 1972, 49(6), 437-438 (Abstract Only).
Acid Hydrolysis in the Homogeneous and Heterogeneous Phase in the Sugar Industry; Szetli, Jozsef, et al. 1971, 24(5), 181-9 (Abstract Only).
Hydrolysis of Sucrose, Raffinose or Stachyose at pH Values Corresponding to Gastic Acidity; Kasai, Tadashi, et al., Eiyo to Shokuryo, 1971, 24(8), 442-5 (Abstract Only).
Mechanism of the Acid Hydrolysis of Saccharose and Raffinose; Szejtli, Jozsef, et al., Acta Chimica Academiae Scientiarum Hungaricae, 1970, 66(2), 213-27 (English) (Abstract Only).
Clean Conversion of Cellulose into Fermentable Glucose, Yong Sun,Junping Zhuang, Lu Lin, Pingkai Ouyang, Biotechnology Advances 27 (2009) 625-623.
Studies on Enzyme Action, XL-Hydrolysis of Raffinose by Acids and Enzymes, H.E. Armstrong, et al., International Catalogue of Scientific Literature, Apr. 2, 1908.
Seasonal Variation of Saccharides and Furfural in Atmospheric Aerosols at a Semi-Urban Site, Aerosol and Air Quality Research, Swithawirat, et al. 15:821-832, 2015.
Acid-Catalyzed conversion of Mono- and Poly-Sugars into Platform Chemicals: Effects of Molecular Structure of Sugar Substrate, Xun Hu, Liping Wu, Yi Wang, Yao Song, Daniel Mourant, Richard Gunawan, Mortaza Gholizadeh, Chun-Zhu Li, Bioresource Technology 133 (2013) 469-474.
New Polystyrene Sulfonic Acid Resin Catalysts with Enhanced Acidic and Catalytic Properties, P.F. Siril, et al. Journal of Molecular Catalysis A: Chemical 279 (2008) 63-68.

(Continued)

*Primary Examiner* — Yate' K Cutliff
(74) *Attorney, Agent, or Firm* — Greer, Burns & Crain, Ltd.

(57) ABSTRACT

Unique methods have been developed to convert polysaccharides into value-added products, such as levulinic acid and alkyl levulinates. The polysaccharides are heated in the presence of water, an alcohol, and an acid to cleave the polysaccharide, and the resulting monosacchrides or monosaccharide acetals or both are contacted with an acid in the presence of an alcohol at a higher temperature. Useful acids include Brønsted acid catalysts and Lewis acid catalysts including mineral acids, metal halides, immobilized heterogeneous catalysts functionalized with a Brønsted acid group or a Lewis acid group, or combinations thereof.

18 Claims, No Drawings

(56) References Cited

OTHER PUBLICATIONS

Mediating Acid-Catalyzed Conversion of Levoglucosan into Platform Chemicals with Various Solvents, Xun Hu, et al., Green Chemistry, 2012, 14, 3087.

Hydrolysis of Cellulose by Amorphous Carbon Bearing SO3H, COOH, and OH Groups, Satoshi Suganuma, et al., Materials and Structures Laboratory, Tokyo Institute of Technology, published on web Aug. 29, 2008.

Investigation of Acid-Catalytic Conversion of Carbohydrates in the Presence of Aliphatic Alcohols at Mild Temperatures, V.E. Tarabanko, et al., Chemistry for Sustainable Development, 13 (2005), 551-558.

Preparation, Characterization and Catalytic Properties of S2082-ZrO2—CeO2 Solid Superacid Catalyst, Fan Goudong, et al., Science Direct Journal of Rare Earths, vol. 27, No. 3, Jun. 2009, p. 437.

Dehydration Reactions of Fructose in Non-aqueous Media, Brown, David W., et al., J. Chem. Tech. Biotechnol. 1982, 32, 920-924.

Catalytic Conversion of Cellulose to Levulinic Acid by Metal Chlorides, Lincai Peng, et al., Molecules, State Key Laboratory of Pulp and Paper Engineering, South China University of Technology, Guangzhou 510640, Guangdon, China, Aug. 2, 2010.

Zeolite H-USY for the Production of Lactic Acid and Methyl Lactate from C3-Sugars, Ryan M. West, et al., Journal of aatalysis 269, (2010), 122-130.

Tin Catalyzed Conversion of Trioses to Alkyl Lactates in Alcohol Solution, Yukiko Hayashi, et al., The Royal Society of Chemistry, Chem. Commun. 2005, 2716-2718.

Grafting SnCL4 Catalysts as a Novel Solid Acid for the Synthesis of 3-Methylbut-3-en-1-ol, Min Ji, et al., Catalysis Today, 173 (2011) 28-31.

Mechanism of Levulinic Acid Formation, Jaroslav Horvat, et al., Tetrahedron Letters, vol. 26, No. 17, pp. 2111-2114, 1985.

Conversion of Carbohydrates and Lignocellulosic Biomass into 5-Hydroxymethylfurfural using AlC13 6H20 Catalyst in a Biphasic Solvent System, Yu Chang, et al., Green Chem. 2012, 14, 509.

Reaction Pathways of Glucose During Esterification: Effects of Reaction Parameters on the Formation of Humin Type Polymers, Xun Hu, et al., Bioresource Technology 102 (2011) 10104-10113.

* cited by examiner

METHODS OF MAKING LEVULINIC ACID AND ALKYL LEVULINATES FROM SACCHARIDES

BACKGROUND OF THE INVENTION

Monosaccharides and polysaccharides such as fructose, glucose and sucrose are abundant materials that can potentially serve as sources of valuable commercial biobased products or intermediates to prepare such products. By biobased, we mean prepared from a plant or animal source. However, monosaccharides such as fructose and glucose are also food components, so conversion of these materials to industrial usage reduces the availability of these saccharides to serve as food stocks. Thus, there is a need to use non-edible saccharides for the production of industrial products.

Soy molasses is a high volume and non-edible byproduct obtained from the production of soy protein isolate and soy protein concentrates from soybeans. It is used mainly for animal feed. Soy molasses is typically produced as about a 50-60% solids soy molasses solution. Sugars constitute about 62 percent of these solids. Sucrose (a disaccharide composed of fructose and glucose), raffinose (a trisaccharide composed of fructose, glucose and galactose), and stachyose (a tetrasaccharide composed of the same monosaccharides) constitute about 96% of the sugar fraction while the monosaccharides fructose and glucose comprise the rest. Saponins which constitute up to about 15% of the solid fraction also contribute saccharides to this composition. Currently, some producers ferment the soy molasses solution to produce methane that is used as a fuel.

Soy molasses could serve as a source for producing value-added biobased products which would provide more value than using it as a fuel.

EP 2184270 reports the conversion of glucose, fructose, xylose and sucrose to racemic methyl lactate in yields of 40-60% when these sugars are heated to 160° C. in the presence of methanol and relatively high concentrations of zeolite tin-beta. This zeolite has tin (IV) molecularly incorporated in its structure. The article "Tin-catalyzed conversion of trioses to alkyl lactates in alcohol solutions", Chem. Commun. 2005, 2716-2718 (Y. Hayashi and Y. Sasaki) described the conversion of dihydroxyacetone (DHA) and glyceraldehyde to alkyl lactates with about 90% yield when heated to 90° C. with primary alcohols in the presence of tin(II) and tin(IV) chloride catalysts. The article "Zeolite H-USY for the production of lactic acid and methyl lactate from C3-sugars", J. Catalysis 2010, 269, 122-130 (R. M. West, et al.) demonstrated that a zeolite with a low Si/Al composition (Zeolyst-Y) was effective in catalyzing the reaction of DHA and glyceraldehyde with methanol to form methyl lactate when heated to 115° C. when using this zeolite catalyst at relatively high concentrations. However, this catalyst lost activity with continued use due to coking, which implies that it would have limited use in a commercial process for converting DHA to alkyl lactates.

The article "Catalytic conversion of cellulose to Levulinic acid by metal chlorides, Molecules 2010, 15, 5258-5272 (L. Peng, et al.) demonstrated that transition metal chlorides, especially chromium(III) chloride, and aluminum chloride exhibit catalytic activity in converting cellulose and glucose to levulinic acid in 55-65% yield when heated to 200° C. in water. A disadvantage of this process is that the levulinic acid is produced as a very dilute aqueous solution so the relatively high cost to evaporate water detracts from the economics of this process.

In "Dehydration of fructose in non-aqueous media", D. W. Brown, et al, Chem. Tech. Biotechnol, 1982, 32, 920, fructose was heated in lower alcohols such as methanol in the presence of Amberlyst-15. A yield of 43% 5-methoxymethyl-2-furfural (methoxy HMF) and 47% methyl levulinate was obtained in methanol. The selectivity in making methyl levulinate was only about 42% (where yield equals conversion times selectivity). Furthermore, when other products such as methoxy HMF are made, a fractionation scheme must be developed to remove the other products, which increases the cost of the process.

There is a need for economical processes of converting non-edible saccharides into useful industrial products.

SUMMARY OF THE INVENTION

Processes have been developed to convert polysaccharides to at least one of levulinic acid and alkyl levulinates.

One aspect of the invention is a method of making at least one of levulinic acid and alkyl levulinates. In one embodiment, the method includes heating a polysaccharide to a temperature in a range of about 50° C. to about 120° C. in the presence of water, a first alcohol, and a first acid to cleave the polysaccharide into at least one monosaccharide or monosaccharide acetal or both. The at least one monosaccharide or monosaccharide acetal or both is contacted with a second acid in the presence of a second alcohol at a temperature in a range of about 100° C. to about 200° C. to form a reaction mixture comprising the at least one of the levulinic acid and the alkyl levulinate. There is a temperature difference of at least 10° C. between the temperature at which the polysaccharide is heated and the temperature at which the monosaccharide is contacted.

Another aspect of the invention is a method of making at least one of monosaccharides or monosaccharide acetals or both. In one embodiment, the method includes heating a polysaccharide to a temperature in a range of about 50° C. to about 120° C. in the presence of water, an alcohol, and an acid to cleave the polysaccharide into at least one monosaccharide or monosaccharide acetal or both.

DETAILED DESCRIPTION OF THE INVENTION

Processes have been developed to convert polysaccharides to levulinic acid and levulinic acid esters, as well as lactic acid, lactic acid esters, and 5-hydroxymethyl-2-furfural (HMF).

Lactic acid is listed by the Department of Energy (DOE) as one of the top-30 biobased intermediates to prepare food additives, detergents, biobased solvents as well as polylactic acid (which requires L-lactic acid). Almost all lactic acid used today is produced from the fermentation of glucose, which makes lactic acid a target of the "food for industrial use" controversy.

Levulinic acid is listed by the DOE as one of the top-10 biobased intermediates, and its uses include PVC plasticizers, lubricants, surfactants and solvents. Levulinic acid can also be readily converted to methyl tetrahydrofuran which is used as a gasoline oxygenate, while esters of levulinic acid are being increasingly used as diesel fuel oxygenates. The main levulinic acid production process involves heating cellulosic feedstocks to about 200-220° C. in the presence of sulfuric acid to produce levulinic acid and formic acid in yields of 50% and 20%, respectively with a 30% yield of char.

Although not wishing to be bound by theory, it is believed that levulinic acid and levulinic esters are formed by the acid catalyzed dehydration of monosaccharides in water and alcohols in a process that involves formation of the intermediate HMF. HMF then undergoes rehydration in converting to levulinic acid that is partially esterified to levulinate esters in the presence of solvent alcohols and water. Polysaccharides have to be cleaved into monosaccharides to be converted to levulinic acid and levulinic esters.

While the formation of lactic acid and lactic esters is believed to proceed by a different mechanism (which involves a reverse aldol cleavage to $C_3$ components), some Lewis acid catalysts can generate both levulinic acid and lactic acid and their esters.

Moreover, the process can be stopped with the production of the monosaccharides and/or monosaccharide acetals, if desired, which can then be used to produce other products.

Humins are non-desired polymeric byproducts that are formed by the acid-catalyzed cross-reaction of non-reacted sugars with the initially formed HMF. Both soluble and insoluble humins are formed, and their presence is readily indicated by their deep black color. It is desirable to minimize the amount of humins produced in the reaction.

A polysaccharide pre-hydrolysis procedure was previously used which involved subjecting the polysaccharides to acid catalyzed hydrolysis in the presence of water and in the absence of alcohol, after which an alcohol was added before further heating the mixture to a higher temperature.

However, it was found that, when employing an acid-catalyzed pre-hydrolysis of soy molasses polysaccharides to generate monosaccharides which were then reacted with added alcohol and then converted to levulinic acid and alkyl levulinates (as described in U.S. application Ser. No. 14/453,426), either a very low yield increase or a yield reduction was observed, depending on reaction conditions. Consequently, methods for improving the conversion of polysaccharides to levulinic acid and alkyl levulinates were developed.

A process was developed which involved heating the polysaccharide in the presence of water, an alcohol, and a first acid at a first (lower) temperature to cleave the polysaccharide into at least one monosaccharide or monosaccharide acetal or both, followed by contacting the contacting the at least one monosaccharide or monosaccharide acetal or both with a second acid in the presence of a second alcohol at a second (higher) temperature. The process results in improved conversion of polysaccharides to levulinic acid and alkyl levulinate.

Although not wishing to be bound by theory, it is believed that a reason only modest amounts of levulinic acid and alky levulinate were obtained from soy molasses polysaccharides using the earlier developed pre-hydrolysis process was that even at the pre-hydrolysis temperature, the resulting monosaccharides were starting to dehydrate to HMF, which then reacted with unreacted monosaccharides to form humin polymers. It is believed that the presence of alcohol at this stage may inhibit this polymerization reaction because the alcohol may react with the aldehyde groups of both the monosaccharides to form monosaccharide acetals and HMF to form HMF acetals. In addition, the alcohol present during the first step may directly cleave the intermolecular acetal linkages in polysaccharides to form monosaccharide acetals by a process known as transacetalation. It is believed that monosaccharide acetals derived from the added alcohol can be hydrolyzed to the monosaccharide, and this species is readily dehydrated to HMF which undergoes rehydration to form levulinic acid. The levulinic acid which is formed is then partially esterified to levulinate esters in the presence of solvent alcohols and water. It is believed that monosaccharide acetals can undergo acid-catalyzed elimination of alcohol to generate carbocations that initiate double bond formation involved in the formation of HMF, which is hydrated to form levulinic acid. The levulinic acid is then partially esterified to form levulinate esters in the presence of solvent alcohols and water.

The polysaccharides can be disaccharides, trisaccharides, tetrasaccharides, or other higher polysaccharides, such as cellulose, hemicellulose, and starch. Suitable polysaccharides include, but are not limited to, sucrose, raffinose, stachyose, galactose, maltose, cellobiose, melibiose, cellulose, starch, other polysaccharides, or combinations thereof. The saccharides can be edible or non-edible.

The polysaccharides may contain alpha and/or beta(1→4) acetal linkages and/or alpha(1→6) acetal linkages. The alpha(1→4) acetal linkages are more easily cleaved than the alpha(1→6) acetal linkages.

The polysaccharide is cleaved in a first step. By "cleave," we mean that the polysaccharide is converted into a monosaccharide by hydrolysis, and/or converted to a monosaccharide acetal by transacetalation.

In the first step, the polysaccharide is heated to a temperature in a range of about 50° C. to about 120° C. in the presence of water, a first alcohol, and a first acid to convert the polysaccharide into at least one monosaccharide or monosaccharide acetal or both, or about 55° C. to about 120° C., or about 60° C. to about 120° C., or about 65° C. to about 120° C., or about 70° C. to about 120° C., or about 75° C. to about 120° C., or about 80° C. to about 120° C., or about 85° C. to about 120° C., or about 90° C. to about 120° C., or about 95° C. to about 120° C., or about 100° C. to about 120° C., or about 105° C. to about 120° C., or about 110° C. to about 120° C., or about 115° C. to about 120° C., or about 50° C. to about 100° C., or about 55° C. to about 100° C., or about 60° C. to about 100° C., or about 65° C. to about 100° C., or about 70° C. to about 100° C., or about 75° C. to about 100° C., or about 80° C. to about 100° C., or about 85° C. to about 100° C., or about 90° C. to about 100° C., or about 95° C. to about 100° C., or about 50° C. to about 115° C., or about 50° C. to about 110° C., or about 50° C. to about 105° C., or about 50° C. to about 100° C., or about 50° C. to about 95° C., or about 50° C. to about 90° C., or about 50° C. to about 85° C., or about 50° C. to about 80° C., or about 50° C. to about 75° C., or about 50° C. to about 70° C., or about 50° C. to about 65° C.

The monosaccharide or monosaccharide acetal or both is contacted with a second alcohol and a second acid at a temperature of at least about 100° C., or at least about 110° C., or at least about 120° C., or at least about 130° C., or in a range of about 100° C. to about 200° C., or about 100° C. to about 190° C., or about 100° C. to about 180° C., or about 110° C. to about 200° C., or about 110° C. to about 190° C., or about 110° C. to about 180° C., or about 120° C. to about 200° C., or about 120° C. to about 190° C., or about 120° C. to about 180° C., or about 130° C. to about 200° C., or about 130° C. to about 190° C., or about 130° C. to about 180° C., or about 140° C. to about 200° C., or about 140° C. to about 190° C., or about 140° C. to about 180° C., or about 150° C. to about 200° C., or about 150° C. to about 190° C., or about 150° C. to about 180° C.

There is a difference in temperature between the first step (heating the polysaccharide to cleave it) and the second step (contacting the monosaccharide or monosaccharide acetal or both) of at least 10° C., or at least 15° C., or at least 20° C., or at least 25° C., or at least 30° C., or at least 35° C., or at least 40° C., or at least 45° C., or at least 50° C.

The first or second alcohol or both can be a monofunctional alcohol, a polyol, or combinations thereof. Suitable monofunctional alcohols include, but are not limited to, methanol, ethanol, 1-propanol, 2-propanol, 1-butanol, 2-butanol, isobutyl alcohol, tert-butyl alcohol, 1-pentanol, 1-hexanol, or combinations thereof. Suitable polyols include, but are not limited to, ethylene glycol, 1,2-propylene glycol, 1,3-propylene glycol, 2-methyl-1,3-propylene glycol, butane-1,2-diol, glycerin, or combinations thereof.

The first and second alcohol can be the same or different. If the first and second alcohols are different, the second alcohol can be added to the mixture formed in the first step without removing the first alcohol, if desired. Typically, the first and second alcohols are the same.

The alcohol can be present in an amount of about 1 ml/g polysaccharide to about 20 ml/g polysaccharide, or about 1 ml/g to about 15 ml/g, or about 1 ml/g to about 10 ml/g, or about 2 ml/g to about 10 ml/g.

The alcohol can be combined with water. The water can be present in an amount of about 5 to about 70% of the alcohol volume, or about 5 to about 65%, or about 5 to about 60%, or about 5 to about 55%, or about 10 to about 70%, or about 10 to about 65%, or about 10 to about 60%, or about 10 to about 55%, or about 15 to about 70%, or about 15 to about 65%, or about 15 to about 60%, or about 15 to about 55%, or about 20 to about 70%, or about 20 to about 65%, or about 20 to about 60%, or about 20 to about 55%, or about 25 to about 70%, or about 25 to about 65%, or about 25 to about 60%, or about 25 to about 55%.

The first or second acids can be the same or different. If the first and second acids are different, the second acid can be added to the mixture formed in the first step without removing the first acid, if desired. Typically, the first and second acids are the same.

Suitable acids include, but are not limited to, mineral acids, solid immobilized heterogeneous catalysts functionalized with a Bronsted or Lewis acid group, or soluble metal halides. Suitable mineral acids include, but are not limited to, $H_2SO_4$, HCl, $HNO_3$, $H_3PO_4$, and combinations thereof. Suitable immobilized heterogeneous catalysts functionalized with a Brønsted acid group include, but are not limited to, at least one of sulfonic acids, and sulfamic acids bound to various immobilized supports comprising at least one of silica gel, silica, an organic resin, and clay such as SiliaBond® Propylsulfonic acid. Suitable immobilized heterogeneous Lewis acid catalysts include SiliaBond® aluminum chloride and metal halides immobilized on suitable supports such as tin(II) chloride bound to silica gel. Suitable soluble metal halide (Lewis acid) catalysts include, but are not limited to, tin(II) halides, such as tin(II) chloride, tin(IV) halides, such as tin(IV) chloride, zinc(II) halides, such as zinc(II) chloride, and aluminum halides, such as aluminum (III) chloride, and combinations thereof.

The amount of mineral acid depends of the strength of the mineral acid, with stronger mineral acids requiring less than weaker mineral acids. The mineral acids can be present in the range of about 0.5 mmole to about 15 mmole acid per gram of polysaccharides, or about 0.5 mmole to about 10 mmole, or about 0.5 mmole to about 8 mmole, or about 1 mmole to about 15 mmole, or about 1 mmole to about 10 mmole, or about 1 mmole to about 8 mmole, or about 2 mmole to about 15 mmole, or about 2 mmole to about 10 mmole, or about 2 mmole to about 8 mmole.

The immobilized heterogeneous catalyst having a Brønsted acid group can be present in an amount of about 0.02 mmole of acidic groups to about 1 mmole of acidic groups per gram of polysaccharide, or about 0.02 mmole to about 0.8 mmole, or about 0.02 mmole to about 0.6 mmole, or about 0.02 mmole to about 0.4 mmole, or about 0.05 mmole to about 1 mmole, or about 0.05 mmole to about 0.8 mmole, or about 0.05 mmole to about 0.6 mmole, or about 0.05 mmole to about 0.4 mmole, or about 0.08 mmole to about 1 mmole, or about 0.08 mmole to about 0.8 mmole, or about 0.08 mmole to about 0.6 mmole, or about 0.08 mmole to about 0.4 mmole, or about 0.1 mmole to about 1 mmole, or about 0.1 mmole to about 0.8 mmole, or about 0.1 mmole to about 0.6 mmole, or about 0.1 mmole to about 0.4 mmole.

The immobilized heterogeneous catalyst having a Lewis acid group can be present in an amount of about 0.08 mmole of acidic groups to about 6 mmole of acidic groups per gram of polysaccharide, or about 0.08 mmole to about 5 mmole, or about 0.08 mmole to about 4 mmole, or about 0.08 mmole to about 3 mmole, or about 0.08 mmole to about 2 mmole, or about 0.08 mmole to about 1 mmole, or about 0.1 mmole to about 6 mmole, or about 0.1 mmole to about 5 mmole, or about 0.1 mmole to about 4 mmole, or about 0.1 mmole to about 3 mmole, or about 0.1 mmole to about 2 mmole, or about 0.1 mmole to about 1 mmole, or about 0.3 mmol to about 6 mmol, or about 0.3 mmole to about 5 mmole, or about 0.3 mmole to about 4 mmole, or about 0.3 mmole to about 3 mmole, or about 0.3 mmole to about 2 mmole, or about 0.3 mmole to about 1 mmole, or about 0.5 mmole to about 6 mmole, or about 0.5 mmole to about 5 mmole, or about 0.5 mmole to about 4 mmole, or about 0.5 mmole to about 3 mmole, or about 0.5 mmole to about 2 mmole, or about 0.5 mmole to about 1 mmole.

The soluble metal catalyst can include one or more of tin(II) halides, tin(IV) halides, zinc(II) halides, or aluminum (III) halides. At high catalyst loadings, tin(II) halide can be present in an amount of about 0.2 to about 0.6 times the weight of the polysaccharide, tin(IV) halide can be present in an amount of about 0.2 to about 0.6 times the weight of the saccharide, and zinc(II) halide can be present in an amount about 20 to about 80% of a weight of the saccharide. The low catalyst loading is about 0.01 to about 0.2 times the weight of the saccharide, or about 0.01 to about 0.1 times the weight of saccharide. For example, tin(II) halide can be present in an amount of about 0.02 to about 0.04 times the weight of the saccharide, tin(IV) halide can be present in an amount of about 0.02 to about 0.06 times the weight of the saccharide, zinc(II) halide can be present in an amount about 0.02 to about 0.4 times a weight of the saccharide. The aluminum(III) halide can be present in the amounts indicated above for the tin and zinc halides.

The total reaction time is generally at least about 3 hr, or at least about 5 hr, or at least about 6 hr, or at least about 8 hr, or at least about 10 hr, or at least 12 hours, or at least 14 hours, or in the range of about 3 hr to about 50 hr, or about 3 hr to about 40 hr, or about 3 hr to about 30 hr, or about 3 hr to about 24 hr, or about 3 hr to about 20 hr, or about 3 hr to about 15 hr, or about 3 hr to about 12 hr. The first step may be about the same length as the second step, although it could be longer or shorter if desired. The first or the second step or both could be in the range of about 1.5 to about 25 hr, or about 1.5 to about 20 hr, or about 1.5 to about 15, or about 1.5 to about 12 hr, or about 1.5 to about 10 hr, or about 1.5 to about 7.5 hr, or about 1.5 to about 6 hr.

In some embodiments, the process involves forming two phases. An aqueous solution of polysaccharides is contacted with an alcohol having a solubility in water of less than 10 wt %, or less than 5 wt %, or less than 2.5 wt %, or less than 1 wt %. Suitable alcohols include, but are not limited to, 1-butanol, 1-pentanol, 1-hexanol, or combinations thereof.

In some embodiments, the starting material is an aqueous solution of polysaccharide containing at least about 5 g polysaccharide/100 ml of aqueous alcoholic solvent of at least one polysaccharide is used, or at least about 10 g polysaccharide/100 ml of aqueous alcoholic solvent, or at least about 15 g polysaccharide/100 ml of aqueous alcoholic solvent, or at least about 20 g polysaccharide/100 ml of aqueous alcoholic solvent, or at least about 25 g polysaccharide/100 ml of aqueous alcoholic solvent, or at least about 30 g polysaccharide/100 ml of aqueous alcoholic solvent, or at least about 35 g polysaccharide/100 ml of aqueous alcoholic solvent, or at least about 40 g polysaccharide/100 ml of aqueous alcoholic solvent, or at least about 50 g polysaccharide/100 ml of aqueous alcoholic solvent. The aqueous solution of polysaccharide containing at least about 5 g polysaccharide/100 ml of aqueous alcoholic solvent of at least one polysaccharide can be one or more of soy molasses, sorghum juice, beet juice, sugar cane, molasses derived from the purification of beet sugar, and molasses derived from the purification of sugar cane sugar. The catalyst comprises a Brønsted acid or a Lewis acid. Examples of suitable catalysts consist essentially of mineral acids, immobilized heterogeneous catalyst functionalized with a Brønsted acid group or a Lewis acid group, and metal halide catalysts, or combinations thereof.

The aqueous solution can be heated using thermal heating, and/or microwave heating, alone or in combination with sonication, or other suitable heating methods known to those of skill in the art.

In one embodiment, the process can be used to cleave polysaccharides to form monosaccharides and monosaccharide acetals by only performing the first step, i.e., heating a polysaccharide to a temperature in a range of about 50° C. to about 120° C. in the presence of water, a first alcohol, and a first acid to cleave the polysaccharide into at least one monosaccharide or monosaccharide acetal or both. These can be used to produce other products including, but not limited to, lactic acid, lactic acid esters, HMF, and the like.

The reaction can be stopped at this stage by conducing the reaction under dehydration conditions to minimize or avoid rehydration of the HMF.

Another option is to limit the reaction time so that there is not sufficient time for levulinic acid to form from rehydration of HMF. The reaction times would be less than those described above (e.g., toward the lower end of the ranges given above).

The reaction temperatures would similar to those listed above. The temperatures may be toward the higher end of the ranges.

The alcohols and acids are those described above.

Conversion of the monosaccharides and/or monosaccharide acetals to lactic acid and/or lactic acid esters can be achieved using a Lewis acid catalyst. In embodiments where a Brønsted acid catalyst is used to cleave the polysaccharide, the Brønsted acid catalyst may need to be removed before adding the Lewis acid catalyst. It may be desirable to use a Lewis acid catalyst to cleave the polysaccharide and to form the lactic acid and/or lactic acid ester. Suitable Lewis acid catalysts are described above.

EXAMPLES

Example 1

The starting material was 48.40 g of soy molasses (40% water) which contains 20.79 g sugars (3.59% fructose, 1.56% glucose, 54.58% sucrose, 6.71% raffinose (a trisaccharide), and 33.57% stachyose (a tetrasaccharide). This means that 94.86% of all the sugars are polysaccharides.

The alcohol (76.7-77.8 g) was methanol.

The acid (8.10-8.26 g) was concentrated sulfuric acid.

In Runs 1-3, 26.73 g of water was added. In Run 4, 48.08 g of water was added, in Run 5, 48.14 g was added, and in Run 6, 48.05 g was added.

In Runs 1 and 4, no pre-hydrolysis was used. The soy molasses was mixed with water, alcohol, and acid, and the mixture was heated for 12 hr at 150° C. (no pre-hydrolysis).

In Runs 2 and 5, a two step process with a pre-hydrolysis step similar to the process described in U.S. application Ser. No. 14/453,426 (Prehydrolysis process 1) was employed. In this case, the soy molasses was mixed with water and acid, and heated at 100° C. for 6 hr; then methanol was added, and the mixture was heated at 150° C. for 6 hr.

In Runs 3 and 6, the modified pre-hydrolysis/transacetalation step of the present invention was used. In this case, the soy molasses was mixed with water, methanol, and acid, and the mixture was heated at 100° C. for 6 hr; then the mixture was heated at 150° C. for 6 hr.

The results are shown in Table 1.

TABLE 1

| Run No. | Total Water (g) | Reaction Sequence | Total Reaction Time (hr) | % Conversion to Levulinic Acid + Methyl Levulinate |
|---|---|---|---|---|
| 1 | 26.73 | No pre-hydrolysis. | 12 | 49.8 |
| 2 | 26.73 | Pre-hydrolysis process 1 | 12 | 51.2 |
| 3 | 26.73 | Modified pre-hydrolysis/ transacetalation | 12 | 65.5 |
| 4 | 48.08 | No pre-hydrolysis | 12 | 58.3 |
| 5 | 48.14 | Pre-hydrolysis process 1 | 12 | 52.8 |
| 6 | 48.05 | Modified pre-hydrolysis/ transacetalation | 12 | 62.1 |

Runs 1-3—Lower Amount of Water Added

Run 1, which had no pre-hydrolysis, had a conversion of 49.8%. Run 2, which used pre-hydrolysis process 1, had a conversion of 51.2% which represents a very modest increase of 1.4 percentage points over Run 1. Run 3, using the modified pre-hydrolysis/transacetalation step, had a conversion of 65.5%, which is 14.3 percentage points higher than observed for pre-hydrolysis process 1.

Runs 4-6—Higher Amount of Water Added

In Run 4, in which no-pre-hydrolysis was employed, the conversion was 58.3%, which is an appreciable increase over Run 1 when using almost twice as much water as in Run 1. Presumably, the extra water in Run 4 along with the same amount of methanol as in Run 1 provided more effective in-situ polysaccharide hydrolysis in the course of this reaction compared to Run 1. It is interesting that pre-hydrolysis process 1 in Run 5, which employed increased water but lacked methanol during the pre-hydrolysis step, had a lower conversion than Run 4 which did not employ pre-hydrolysis. These results tend to support the beneficial effect of methanol during in-situ hydrolysis in Run 4. In Run 6, the conversion using the modified pre-hydrolysis/transacetalation step provided the highest conversion in the higher water runs (62.1 percent). This conversion was 9.3 percentage points higher than pre-hydrolysis process 1 in Run 5, and 3.8 percentage points higher than in Run 4 where pre-hydrolysis was not performed.

Under relatively low water conditions, the modified pre-hydrolysis/transacetalation resulted in significantly higher conversion of a high polysaccharide feedstock to levulinic acid and methyl levulinate compared to processes not employing pre-hydrolysis or employing pre-hydrolysis process 1.

Under appreciably higher water conditions, the modified pre-hydrolysis/transacetalation also provided higher conversions than the other two methods.

Example 2

The testing reported in Example 1 is repeated except that the water content is 5 g, 10 g, 15 g, 20 g, 25 g, 30 g, 35 g, 40 g, and 45 g, and acceptable results are obtained.

Example 3

The testing reported in Examples 1-2 is repeated except that ethylene glycol is used as the alcohol, and acceptable results are obtained.

Example 4

The testing reported in Examples 1-2 is repeated except that a mixture of methanol and ethylene glycol is used as the alcohol, and acceptable results are obtained.

By the term "about," we mean within 10% of the value, or within 5%, or within 1%.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A method of making at least one of levulinic acid, and alkyl levulinate comprising:
   heating a polysaccharide to a temperature in a range of about 50° C. to about 120° C. in the presence of water, a first alcohol, and a first acid to cleave the polysaccharide into at least one monosaccharide or monosaccharide acetal or both;
   increasing the temperature of the at least one monosaccharide or monosaccharide acetal or both and contacting the at least one monosaccharide or monosaccharide acetal or both with a second acid in the presence of a second alcohol at a temperature in a range of about 100° C. to about 200° C. to form a reaction mixture comprising the at least one of the levulinic acid and the alkyl levulinate; and
   wherein there is a temperature difference of at least 10° C. between the temperature at which the polysaccharide is heated and the temperature at which the monosaccharide or monosaccharide acetal or both is contacted.

2. The method of claim 1 wherein the first or second alcohol or both comprises a monofunctional alcohol, a polyol, or both.

3. The method of claim 1 wherein the first and second alcohol are the same.

4. The method of claim 1 wherein the first or second alcohol or both comprises methanol, ethanol, 1-propanol, 2-propanol, 1-butanol, 2-butanol, isobutyl alcohol, tert-butyl alcohol, 1-pentanol, 1-hexanol, or combinations thereof.

5. The method of claim 1 wherein the first or second alcohol or both comprises ethylene glycol, 1,2-propylene glycol, 1,3-propylene glycol, 2-methyl-1,3-propylene glycol, butane-1,2-diol, glycerin, or combinations thereof.

6. The method of claim 1 wherein the first or second acid or both comprises a mineral acid, a metal halide catalyst, an immobilized heterogeneous catalyst functionalized with a Brønsted acid group or a Lewis acid group, or combinations thereof.

7. The method of claim 6 wherein the first or second acid or both is the immobilized heterogeneous catalyst functionalized with the Brønsted acid group or the Lewis acid group, and wherein the immobilized heterogeneous catalyst functionalized with the Brønsted acid group or the Lewis acid group comprises at least one of a metal halide, a sulfonic acid, and a sulfamic acid bound to an immobilized support comprising at least one of silica gel, silica, an organic resin, and clay.

8. The method of claim 6 wherein the first or second acid or both is the mineral acid, and wherein the mineral acid comprises HCl, $H_2SO_4$, $HNO_3$, $H_3PO_4$, or combinations thereof.

9. The method of claim 1 wherein the first and second acid are the same.

10. The method of claim 1 wherein the polysaccharide is sucrose, raffinose, stachyose, galactose, maltose, cellobiose, mellibiose, cellulose, starch, or combinations thereof.

11. The method of claim 1 wherein the polysaccharide contains an alpha(1→4) acetal linkage, a beta(1→4) acetal linkage, an alpha(1→6) acetal linkage, and combinations thereof.

12. The method of claim 1 wherein the polysaccharide comprises at least one of soy molasses, sorghum juice, beet juice, sugar cane, molasses derived from the purification of beet sugar, and molasses derived from the purification of sugar cane sugar.

13. A method of making at least one of levulinic acid and alkyl levulinate comprising:
   heating a polysaccharide to a temperature in a range of about 50° C. to about 120° C. in the presence of water, a first monofunctional alcohol, and a first acid to cleave the polysaccharide into at least one monosaccharide or monosaccharide acetal or both;
   increasing the temperature of the at least one monosaccharide or monosaccharide acetal or both and contacting the at least one monosaccharide or monosaccharide acetal or both with a second acid in the presence of a second monofunctional alcohol at a temperature in a range of about 100° C. to about 200° C. to form a reaction mixture comprising the at least one of the levulinic acid and the alkyl levulinate; and
   wherein there is a temperature difference of at least 10° C. between the temperature at which the polysaccharide is heated and the temperature at which the monosaccharide or monosaccharide acetal or both is contacted.

14. The method of claim 13 wherein the first or second monofunctional alcohol or both comprises methanol, ethanol, 1-propanol, 2-propanol, 1-butanol, 2-butanol, isobutyl alcohol, tert-butyl alcohol, 1-pentanol, 1-hexanol, or combinations thereof.

15. The method of claim 13 wherein at least one of: heating the polysaccharide or contacting the at least one monosaccharide or monosaccharide acetal or both takes place in the further presence of at least one polyol.

16. The method of claim 13 wherein at least one of:
the first and second monofunctional alcohol are the same; and
the first and second acid are the same.

17. The method of claim 13 wherein the first or second acid or both comprises a mineral acid, a metal halide catalyst, an immobilized heterogeneous catalyst functionalized with a Brønsted acid group or a Lewis acid group, or combinations thereof.

18. The method of claim 16 wherein the acid is the immobilized heterogeneous catalyst functionalized with the Brønsted acid group or the Lewis acid group, and wherein the immobilized heterogeneous catalyst functionalized with the Brønsted acid group or the Lewis acid group comprises at least one of a metal halide, a sulfonic acid, and a sulfamic acid bound to an immobilized support comprising at least one of silica gel, silica, an organic resin, and clay.

* * * * *